(12) United States Patent
Vignon et al.

(10) Patent No.: US 11,771,392 B2
(45) Date of Patent: Oct. 3, 2023

(54) MULTI-MODAL IMAGING ALIGNMENT

(71) Applicant: KONINKLIJKE PHILIPS N.V., Eindhoven (NL)

(72) Inventors: Francois Guy Gerard Marie Vignon, Andover, MA (US); Molly Lara Flexman, Melrose, MA (US); Ameet Kumar Jain, Boston, MA (US); Niels Nojhof, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 75 days.

(21) Appl. No.: 16/981,636

(22) PCT Filed: Mar. 19, 2019

(86) PCT No.: PCT/EP2019/056847
§ 371 (c)(1),
(2) Date: Sep. 16, 2020

(87) PCT Pub. No.: WO2019/180023
PCT Pub. Date: Sep. 26, 2019

(65) Prior Publication Data
US 2021/0022698 A1    Jan. 28, 2021

Related U.S. Application Data

(60) Provisional application No. 62/644,644, filed on Mar. 19, 2018.

(51) Int. Cl.
*A61B 6/00* (2006.01)
*A61B 6/12* (2006.01)
(Continued)

(52) U.S. Cl.
CPC .............. *A61B 6/5247* (2013.01); *A61B 6/12* (2013.01); *A61B 6/4417* (2013.01);
(Continued)

(58) Field of Classification Search
CPC ....... A61B 6/5247; A61B 6/12; A61B 6/4417; A61B 8/0841; A61B 8/0883; A61B 8/4245; A61B 8/4416; A61B 8/5261
See application file for complete search history.

(56) References Cited

U.S. PATENT DOCUMENTS

2012/0259237 A1 * 10/2012 Axelrod .............. A61M 5/1452
600/506
2013/0023766 A1     1/2013 Han et al.
(Continued)

FOREIGN PATENT DOCUMENTS

| WO | 2012001548 A1 | 1/2012 |
| WO | 2017089509 A1 | 6/2017 |

OTHER PUBLICATIONS

Gang Gao, "Registration of 3D trans-esophageal echocardiography to X-ray fluoroscopy using image-based probe tracking", 2012, Science Direct, vol. 16, Issue 1 (Year: 2012).*

(Continued)

*Primary Examiner* — Colin T. Sakamoto
*Assistant Examiner* — Tommy T Ly

(57) ABSTRACT

A controller for maintaining alignment of X-Ray imagery and ultrasound imagery includes a memory that stores instructions, and a processor that executes the instructions. When executed by the processor, the instructions cause the controller to execute a process that includes receiving data from an X-Ray system used to perform X-Ray imaging, and receiving data from an ultrasound imaging probe used to perform ultrasound imaging. The process executed by the controller also includes registering imagery based on X-Rays to imagery from the ultrasound imaging probe based on an X-Ray image of the ultrasound imaging probe among the imagery based on X-Rays, and detecting, from the data from the ultrasound imaging probe, movement of the ultrasound imaging probe.

18 Claims, 7 Drawing Sheets

(51) Int. Cl.
*A61B 8/08* (2006.01)
*A61B 8/00* (2006.01)

(52) U.S. Cl.
CPC .......... *A61B 8/0841* (2013.01); *A61B 8/0883* (2013.01); *A61B 8/4245* (2013.01); *A61B 8/4416* (2013.01); *A61B 8/5261* (2013.01)

(56) References Cited

U.S. PATENT DOCUMENTS

| | | |
|---|---|---|
| 2013/0279780 A1 | 10/2013 | Grbic et al. |
| 2014/0142419 A1 | 5/2014 | Shalgi et al. |
| 2015/0065859 A1* | 3/2015 | Hwang .................. A61B 6/037 600/440 |
| 2016/0030008 A1 | 2/2016 | Gerard |
| 2016/0157815 A1* | 6/2016 | Slak ..................... A61B 8/0841 433/29 |
| 2020/0155120 A1* | 5/2020 | Nijhof, Jr. ............ A61B 8/4477 |

OTHER PUBLICATIONS

Hatt et al: "Real-Time Pose Estimation of Devices From X-Ray Images:Application to X-Ray/Echo Registration for Cardiac Interventions"; Medical Image Analysis 34 (2016), pp. 101-108.

PCT/EP2019/056847 ISR & WO, May 14, 2019, 12 Page Document.

Wang et al: "Probe Tracking and Its Application in Automatic Acquisition Using a Transesophageal Ultrasound Robot"; Springer-Verlag Publishers, 2011, 10 Page Document.

\* cited by examiner

MULTI-MODAL IMAGING ALIGNMENT

CROSS-REFERENCE TO PRIOR APPLICATIONS

This application is the U.S. National Phase application under 35 U.S.C. § 371 of International Application No. PCT/EP2019/056847, filed on Mar. 19, 2019, which claims the benefit of Provisional Patent Application No. 62/644, 644, filed on Mar. 19, 2018. These applications are hereby incorporated by reference herein.

BACKGROUND

The Echo Navigator (EchoNav) is a tool in a catheter lab (cathlab) software suite that allows fusing intra-operative X-Ray fluoroscopy images with intra-operative transesophageal echocardiography (TEE) images. The TEE probe is tracked intermittently on X-Ray fluoroscopy, though not continuously due to concerns with exposing patients to too much X-Ray. For high precision two or more X-Ray fluoroscopy projections are initially used to determine the position and orientation of the TEE probe in three-dimensional (3D) space, though only one plane is typically used after initial registration of the X-Ray fluoroscopy to the TEE. The TEE probe is segmented from the X-Ray fluoroscopy imagery and its position and orientation on X-Ray fluoroscopy determined. Based on that, the TEE imagery is overlaid in the correct position on the X-Ray fluoroscopy imagery. The position of the TEE probe is subsequently updated each time a new X-Ray fluoroscopy image (single X-Ray fluoroscopy projection) is acquired.

FIG. 1 shows the known fusion process described above. In FIG. 1, at S101A an X-Ray fluoroscopy projection #1 includes the TEE probe 100. At S101B, an X-Ray fluoroscopy projection #2 also includes the TEE probe 100. At S102, the TEE probe 100 is segmented from the two X-Ray fluoroscopy projections, as this then reflects the isolated positioning and orientation of the TEE probe 100. At S103, the position and orientation of the TEE probe 100 is determined based on the segmentation of the TEE probe 100 from the two X-Ray fluoroscopy projections. At S104, imagery from the TEE probe 100 is overlaid on an X-Ray fluoroscopy image based on the determination of position and orientation of the TEE probe 100.

Since the TEE probe 100 is only tracked using X-Ray fluoroscopy, if no X-Ray fluoroscopy imaging is performed there is no information available to tell the user if the current visualization is valid. Currently, this information may be communicated via color-coding of the TEE probe 100 in a model on an electronic display, so that after a certain amount of time since the last X-Ray fluoroscopy image, the color of the model of the TEE probe 100 turns, e.g., from green to white, indicating that the registration is stale. Additionally, accuracy is currently limited because in subsequent fluoroscopy acquisitions the live X-Ray fluoroscopy image is an X-Ray fluoroscopy projection from a single plane.

Unawareness of the ultrasound imaging probe position at times (such as when no X-Ray fluoroscopy is used) can be an important workflow barrier. The registration of the ultrasound image to the X-Ray fluoroscopy image is not only used to relate the live ultrasound image to the X-Ray fluoroscopy image (e.g. fusion), but also to display annotations that are registered in/on the X-Ray fluoroscopy image back in/on the ultrasound image. When the registration is unknown, annotation may be displayed incorrectly in the ultrasound image which can result in confusion or reduced confidence (even when the status is technically correct). Knowledge of the registration no longer being valid would therefore bring a workflow benefit over current solutions which result from time outs. Compensating for movement of the ultrasound imaging probe could result in even greater benefits.

SUMMARY

According to an aspect of the present disclosure, a controller for maintaining alignment of X-Ray imagery and ultrasound imagery includes a memory that stores instructions, and a processor that executes the instructions. When executed by the processor, the instructions cause the controller to execute a process that includes receiving data from an X-Ray system used to perform X-Ray imaging, and receiving data from an ultrasound imaging probe used to perform ultrasound imaging. The process executed by the controller also includes registering imagery based on X-Rays to imagery from the ultrasound imaging probe based on an X-Ray image of the ultrasound imaging probe among the imagery based on X-Rays, and detecting, from the data from the ultrasound imaging probe, movement of the ultrasound imaging probe.

According to another aspect of the present disclosure, a method for maintaining alignment of X-Ray imagery and ultrasound imagery includes receiving, by a computer that includes a memory that stores instructions and a processor that executes the instructions, data from an X-Ray system used to perform X-Ray imaging. The method also includes receiving, by the computer, data from an ultrasound imaging probe used to perform ultrasound imaging. The method further includes registering imagery based on X-Rays to imagery from the ultrasound imaging probe based on an X-Ray image of the ultrasound imaging probe among the imagery based on X-Rays, and detecting, by the processor and from the data from the ultrasound imaging probe, movement of the ultrasound imaging probe.

According to yet another aspect of the present disclosure, a system for maintaining alignment of X-Ray imagery and ultrasound imagery includes an X-Ray system, an ultrasound imaging probe, and a controller. The X-Ray system generates imagery based on X-Rays. The ultrasound imaging probe generates ultrasound imagery. The controller includes a memory that stores instructions and a processor that executes the instructions. When executed by the processor, the instructions cause the controller to execute a process that includes receiving data from the X-Ray system, and receiving data from the ultrasound imaging probe. The process executed by the controller also includes registering imagery based on X-Rays to imagery from the ultrasound imaging probe based on an X-Ray image of the ultrasound imaging probe among the imagery based on X-Rays, and detecting, from the data from the ultrasound imaging probe, movement of the ultrasound imaging probe.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
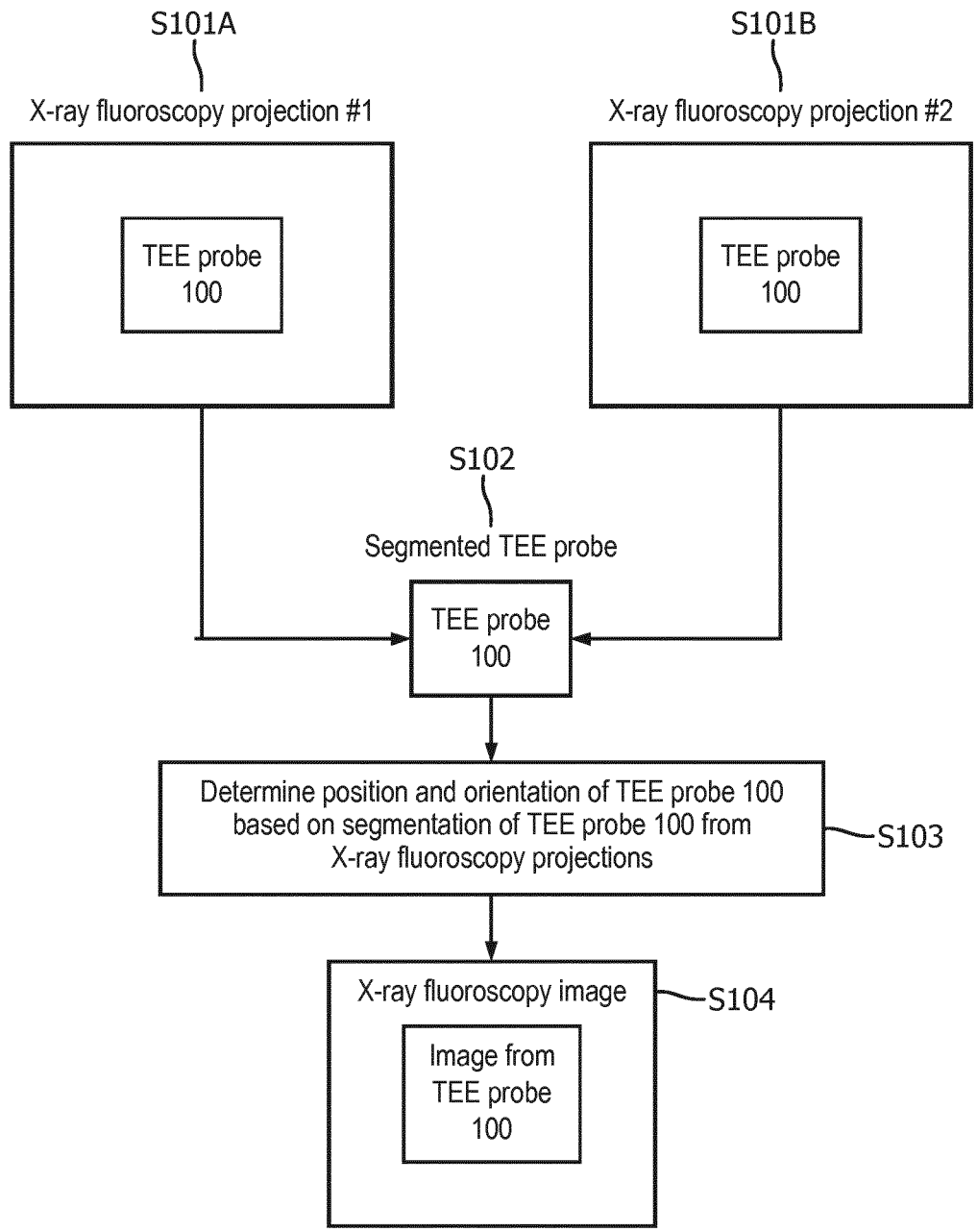
FIG. 1 illustrates a known fusion process for fusing intra-operative X-Ray imagery with intra-operative transesophageal echocardiography (TEE) imagery.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Hereinafter, X-Ray fluoroscopy will be referred to as X-Ray, and ultrasound of any type including TEE will be referred to as ultrasound.

Figure 2A:
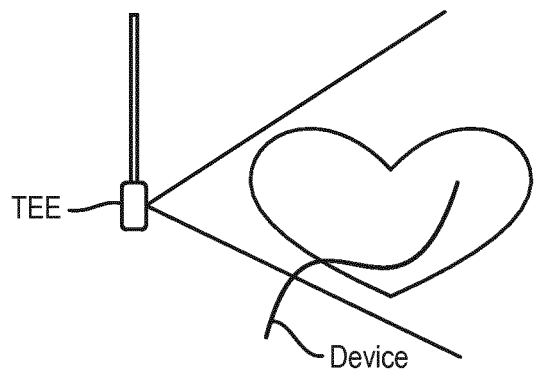
FIG. 2A illustrates multi-modal imaging alignment in an initial view, in accordance with a representative embodiment.
Figure 2B:
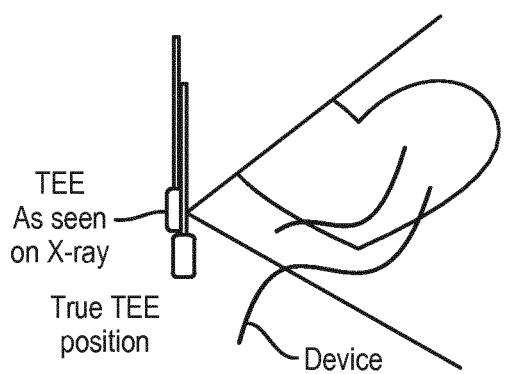
FIG. 2B illustrates multi-modal imaging alignment after movement of an ultrasound imaging probe, in accordance with the representative embodiment of FIG. 2A.
Figure 2C:
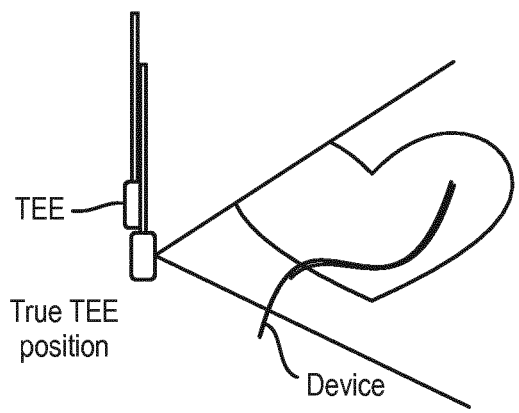
FIG. 2C illustrates multi-modal imaging alignment after compensation for the movement of the ultrasound imaging probe, in accordance with the representative embodiment of FIG. 2A and FIG. 2B.

FIGS. 2A, 2B and 2C are representative of views of an EchoNav software suite in a fusion view.

FIG. 2A illustrates multi-modal imaging alignment in an initial view, in accordance with a representative embodiment.

In FIG. 2A, after fusion of an X-Ray image and an ultrasound image, X-Ray and ultrasound views are aligned. In FIG. 2A, the X-Ray and ultrasound views are images of a heart as well as of an interventional medical device in/on the heart.

FIG. 2B illustrates multi-modal imaging alignment after movement of an ultrasound imaging probe, in accordance with the representative embodiment of FIG. 2A.

In FIG. 2B, after movement of the ultrasound imaging probe, the real-time cardiac (X-Ray) view appears shifted with respect to the previous cardiac (X-Ray) view before the motion occurred. Specifically, in FIG. 2B the higher display of the device is based on the ultrasound and the lower display of the device is the previous X-Ray view before the motion occurred. The difference between the higher display and the lower display of the device is resolved subsequently by the multi-modal imaging alignment.

FIG. 2C illustrates multi-modal imaging alignment after compensation for the movement of the ultrasound imaging probe, in accordance with the representative embodiment of FIG. 2A and FIG. 2B.

In FIG. 2C, motion compensation puts the ultrasound view back in agreement with the previous cardiac (X-Ray) view. In other words, the compensating shown in FIG. 2C and described here and elsewhere herein corrects a registration mismatch between imagery based on X-Rays and imagery from an ultrasound imagery probe.

As shown in FIG. 2B, movement of the ultrasound imaging probe can result in a displacement, misalignment, or other imbalance between imagery from the ultrasound imaging probe and imagery from an X-Ray. In other words, if the ultrasound imaging probe moves between two X-Ray acquisitions, the spatial relationship between the ultrasound imagery and the X-Ray imagery is lost. X-Ray cannot be used constantly due to the radiation exposure to the patient and staff, but constant use of X-Ray would be the only way to recognize the movement previously. Moreover, for some interventions such as some structural heart interventions, X-Ray imaging may not be the main imaging modality. Especially for mitral or tricuspid valve procedures, echo is used mostly for device navigation because the live soft-tissue structures that need to be visualized for treatment cannot be imaged by X-Ray.

As described herein, the ultrasound images can be analyzed to detect motion and indicate to the user that the probe has moved and the registration is no longer accurate. Moreover, as shown in FIG. 2C, the motion can be compensated so at to allow for accurate registration between X-Ray and ultrasound. The compensation of the motion is done without X-Ray, and is instead based on detected ultrasound motion.

Figure 3:
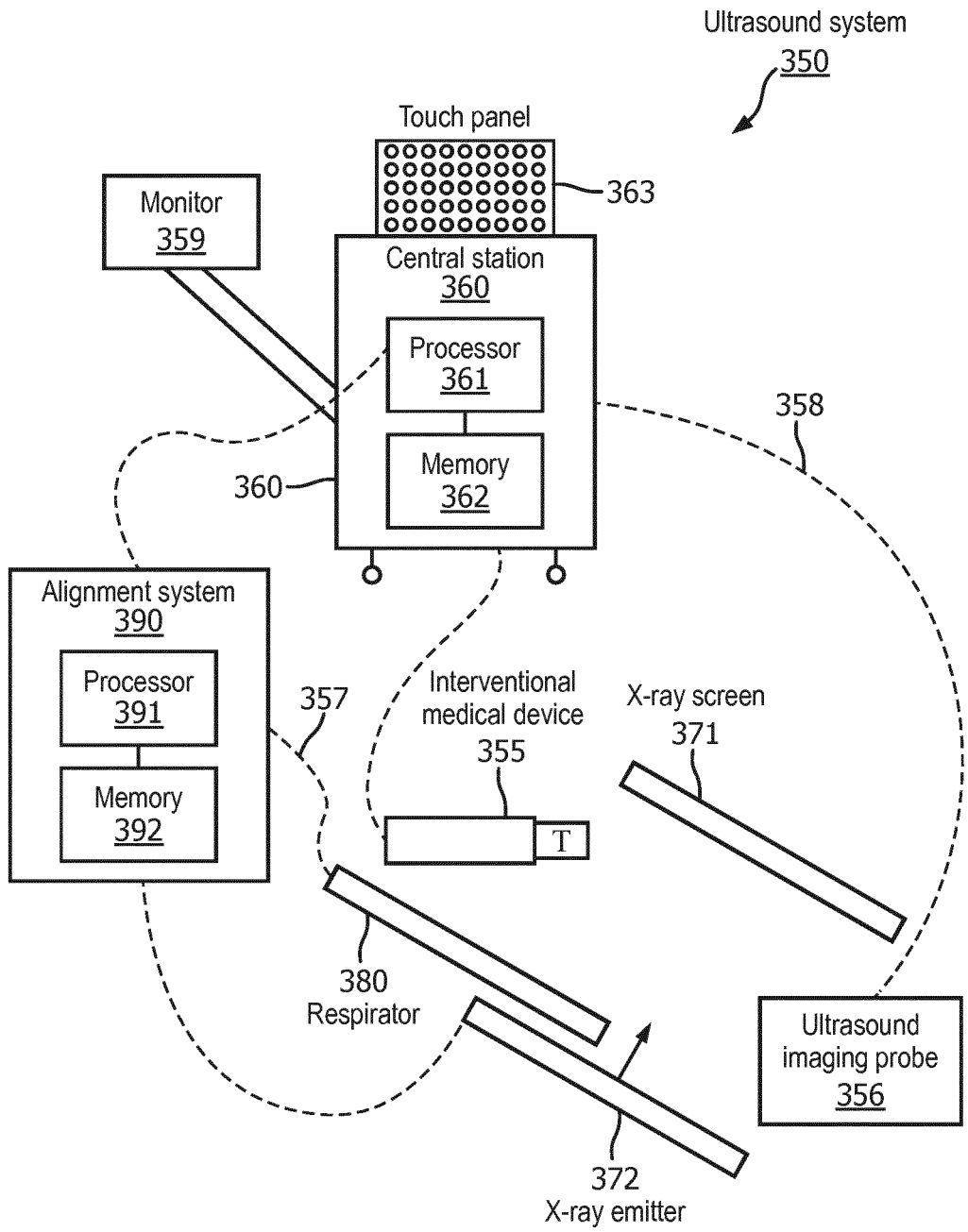
FIG. 3. illustrates a system for multi-modal imaging alignment, in accordance with a representative embodiment.

FIG. 3. illustrates a system for multi-modal imaging alignment, in accordance with a representative embodiment.

In FIG. 3, an ultrasound system 350 includes a central station 360 with a processor 361 and memory 362, a touch panel 363, a monitor 359, an ultrasound imaging probe 356 connected to the central station 360 by a data connection 358 (e.g., a wired or wireless data connection), and an interventional medical device 355 connected to the central station 360 a data connection 357 (e.g., a wired or wireless data connection). The interventional medical device 355 in FIG. 2A includes a sheath S and a wire W.

An X-Ray emitter 372 emits X-Rays towards an X-Ray screen 371. Additionally, a respirator 380 is arranged close to the X-Ray emitter 372.

An alignment system 390 includes a processor 391 and a memory 392. The alignment system 390 receives data from the X-Ray emitter 372, the respirator 380, and the central station 360. The alignment system 390 performs processes described herein by, for example, the processor 391 executing instructions in the memory 392. However, the alignment system 390 may also be implemented in or by the central station 360, or in any other mechanism. The combination of the processor 391 and memory 392, whether in the alignment system 390 or in another configuration, may be considered a "controller" as the term is used herein.

The interventional medical device 355 may include a tool T as shown. The interventional medical device 355 corresponds to the device shown in the various views of FIG. 2A, FIG. 2B and FIG. 2C, and is the subject being aligned from imagery generated by the X-Ray emitter 372 and imagery created by the ultrasound imaging probe 356. Alignment of the different imagery then allows a view from (rather than of) the ultrasound imaging probe 356 to be shown overlaid properly on a view from the X-Ray emitter 372.

By way of explanation, the interventional medical device 355 is placed internally into a patient during a medical procedure. Locations of the interventional medical device 355 can be seen both on imagery generated by the X-Ray emitter 372 and imagery created by the ultrasound imaging probe 356. Alignment of the positioning of the interventional medical device 355 in the different imaging modes is maintained to the extent possible. As described herein, data from the ultrasound imaging probe 356 can be used to detect movement of the ultrasound imaging probe 356, which can be used and useful in variety of ways.

For example, upon detecting movement of the ultrasound imaging probe 356, the movement of the ultrasound imaging probe 356 may be compared against a predetermined threshold. When the movement of the ultrasound imaging probe 356 is determined to exceed the predetermined threshold, a notification can be generated based on detecting the movement and determining that the movement exceeds the predetermined threshold. A notification can be a binary mechanism, such as a warning light or indicator, warning an operator visually that movement has been detected. The notification may also be a variable mechanism such as a warning light that becomes progressively brighter as the movement of the ultrasound imaging probe 356 becomes larger, such that the predetermined threshold may be one of numerous different predetermined thresholds that each corresponds to a different brightness setting, or to a different color of warning light. Thus, the notification can vary based on an amount of movement of the ultrasound imaging probe 356, and is not restricted to a binary mechanism.

The notification may indicate that movement exceeds a certain threshold, and this in turn means that a spatial position of an ultrasound image shown on a screen can no longer be trusted. For example, the ultrasound imaging probe shown on an interface may be colored white or red. The user then has the choice to acquire a new X-Ray image to re-anchor the registration, if needed. As noted above, the user can be given either a binary threshold, or a confidence feedback that can display notifications with different meanings. For example, a notification may be a bar that shows a different shades or brightness levels of color, such as from green meaning that the ultrasound imaging probe is detected and stable, to red meaning that the ultrasound imaging probe has moved and new input is needed.

The respirator 380 can be used to provide input to the alignment system 390. Breathing motion is always present in a live patient, and such breathing motion may be periodic. Accordingly, periodicity due to respiration in the respiratory cycle can be identified and removed, whether due to natural unaided respiration or due to respiration assisted by the respirator 380. Insofar as breathing motion is always present, such breathing motion should be factored out from consideration as the cause of movement of an ultrasound imaging probe 356 that would exceed a threshold and trigger a new X-Ray image acquisition. A four-dimensional (4D) dataset of three-dimensional (3D) breathing motion over time can be used to filter out the breathing motion. A 4D dataset reflects a breathing cycle (respiratory cycle) separate from a cardiac cycle. Alternatively, a time longer than an individual breathing cycle, such as 10 seconds, can be used to perform pattern analysis of the image changes to discriminate between changes due to breathing motion and breathing due to probe motion. The respiratory motion can be compensated based on input received from an external respiration device such as the respirator 380, or from an external sensor that monitors respiration but does not aid the respiration.

Optionally, inputs from the respirator 380 can be used directly, such as when a patient is under general anesthesia. Alternatively, a belt can be used for breathing motion estimation. Inputs from either a respirator 380 or an alternative belt can be fed to the alignment system 390 to discriminate between breathing motion and ultrasound imaging probe 356 motion. The motion pattern can be measured on ultrasound echo images, and cross-correlation analysis (e.g., normalized cross-correlation) can be performed on the measured motion. If the cross-correlation between the estimated temporal motion pattern from the ultrasound echo images and the inputs of the respirator 380 or alternative belt/belt is high, then the estimated motion is likely to be mostly breathing.

The amount of movement of the ultrasound imaging probe 356 may also be measured so as to determine how much the movement is to be compensated. For example, motion detection can be achieved by change detection in the ultrasound cineloops. A cineloop is a related series of images in a period, stored digitally as a sequence of individual frames. Therefore, movement of the ultrasound imaging probe can be detected based on analysis of a cineloop from the ultrasound imaging probe.

For robustness, the analysis to determine the amount of movement may be done cardiac cycle by cardiac cycle. A heart can be imaged in three dimensions, and over time this can reveal a cardiac cycle. Each cardiac cycle imaged in three dimensions over time is a four-dimensional (4D) dataset. That is, a three-dimensional cardiac cycle identified over time is a four-dimensional cardiac cycle, and movement of the ultrasound imaging probe can be detected between such four-dimensional cardiac cycles. 4D datasets of successive cardiac cycles can be compared to detect movement including the amount of movement.

For example, ultrasound imagery from different cycles can be compared using sum of square differences or other similar metrics after spatio-temporal low-pass filtering. Alternatively, an amount of change in a registration matrix may reflect characteristics such as rotation and/or translation of the anatomy. Amounts of movement can be measured relative to anatomical landmark. Amount of change may also be measured from segmentations of the anatomy. Moreover, an amount of change can be measured from a registration matrix that reflects the characteristics such as rotation and/or translation of the anatomy, but fit of a heart model to the 3D ultrasound dataset.

6-DOF (six degrees of freedom) motion estimation can be performed based on the four-dimensional ultrasound cardiac cineloops (or X-plane+time). The six degrees of freedom include three axes of translation and three axes of rotation. Here, the heart may be used as a fixed beacon, and apparent motion of the heart inside of the field of view corresponds to motion of the field of view around the heart. That is, apparent motion of the heart inside of the field corresponds to probe motion that affects the field of view around the heart, so this can be used as the basis of determining that motion of the ultrasound imaging probe has occurred, as well as subsequent compensation. Known motion estimation and compensation techniques can be used to keep the heart position steady on the X-Ray overlay, such that the position of the ultrasound sector on the X-Ray image will be adjusted, and may be offset from the position of the ultrasound imaging probe as seen on X-Ray, as the latter corresponds to an outdated X-Ray image. The offset is shown in FIGS. 2B and 2C. An indication can be provided to indicate that the ultrasound imaging probe has moved and a new X-Ray image should be again acquired so that registration can be updated.

In another example, upon detecting movement of the ultrasound imaging probe 356, the movement of the ultrasound imaging probe 356 may be compensated to maintain alignment between the imagery based on X-Rays from the X-Ray emitter and the imagery from the ultrasound imaging probe 356.

Additionally, movement of the interventional medical device 355 can be excluded from the motion analysis to avoid complications. For example, movement of the interventional medical device 355 within the ultrasound volume can create a false-positive indication that the ultrasound imaging probe 356 has moved. For this reason, an X-plane or 4D dataset may be used to provide more robustness. Alternatively, model-based registration techniques can be used to enhance robustness. If the interventional medical device 355 is tracked using one of many methods, including image-based segmentation or navigation, then the position of the interventional medical device 355 in the ultrasound volume is known. As examples of instrument tracking systems, an electromagnetic (EM) tracking system uses a field generator and tracked sensor coils. InSitu tracking systems use passive ultrasound sensors that detect ultrasounds and send a signal based on the detected ultrasound signal which can be used to identify location. As a result, the portion of the ultrasound image that surrounds the device can be excluded from the motion detection algorithm. For example, a generic three-dimensional shape such as a barrel can or box can be tightly superimposed on the interventional medical device 355 in the ultrasound image to minimize the excluded area FIG. 4 illustrates a general computer system, on which a method of multi-modal imaging alignment can be implemented, in accordance with a representative embodiment.

The computer system 400 can include a set of instructions that can be executed to cause the computer system 400 to perform any one or more of the methods or computer based functions disclosed herein. The computer system 400 may operate as a standalone device or may be connected, for example, using a network 401, to other computer systems or peripheral devices. Any or all of the elements and characteristics of the computer system 400 in FIG. 4 may be representative of elements and characteristics of the central station 360, the alignment system 390, the ultrasound imaging probe 356, the ultrasound system 350, or other similar devices and systems that can include a controller and perform the processes described herein.

In a networked deployment, the computer system 400 may operate in the capacity of a client in a server-client user network environment. The computer system 400 can also be fully or partially implemented as or incorporated into various devices, such as a control station, imaging probe, passive ultrasound sensor, stationary computer, a mobile computer, a personal computer (PC), or any other machine capable of executing a set of instructions (sequential or otherwise) that specify actions to be taken by that machine. The computer system 400 can be incorporated as or in a device that in turn is in an integrated system that includes additional devices. In an embodiment, the computer system 400 can be implemented using electronic devices that provide video or data communication. Further, while the computer system 400 is illustrated, the term "system" shall also be taken to include any collection of systems or sub-systems that individually or jointly execute a set, or multiple sets, of instructions to perform one or more computer functions.

Figure 4:
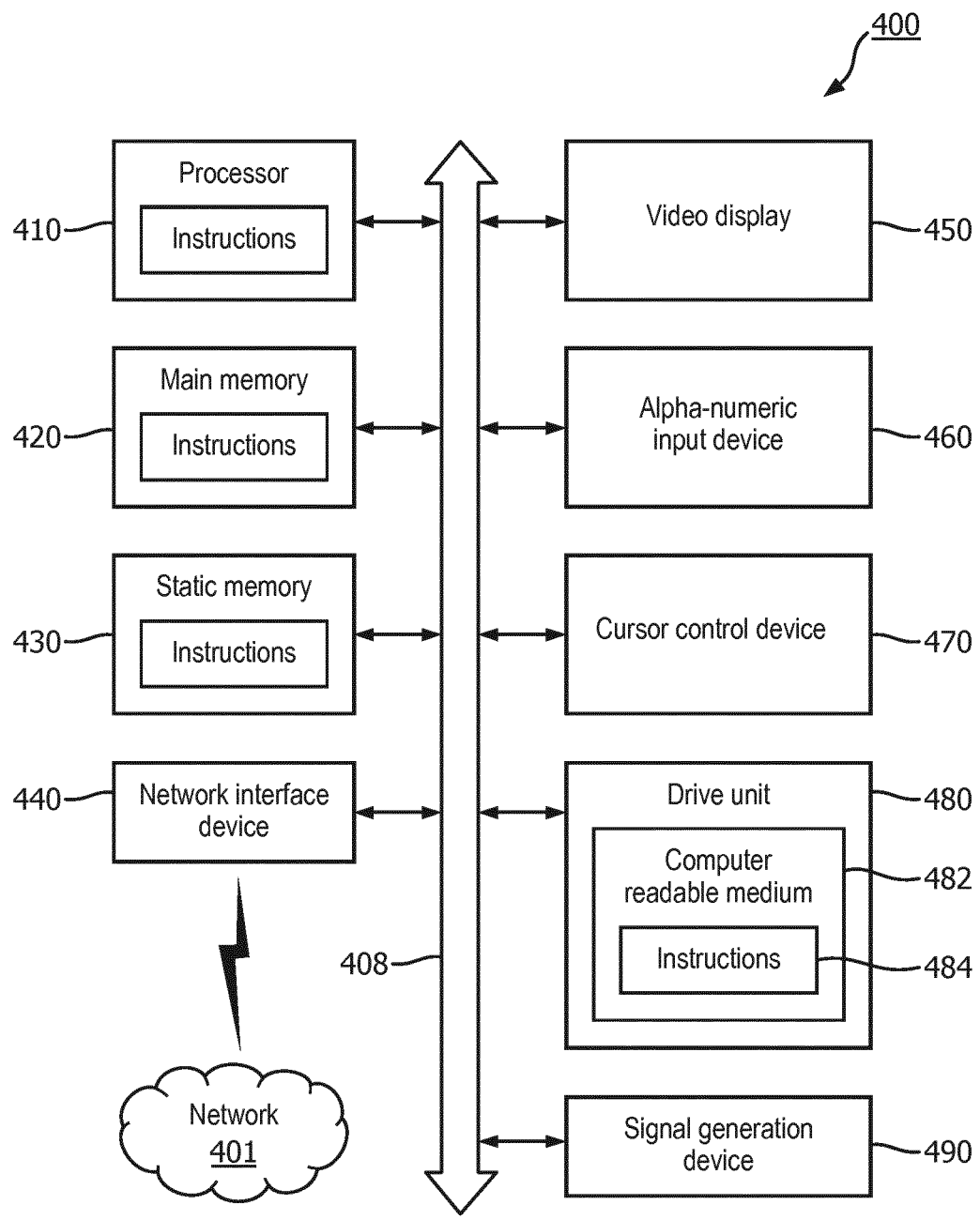
FIG. 4 illustrates a general computer system, on which a method of multi-modal imaging alignment can be implemented, in accordance with a representative embodiment.

As illustrated in FIG. 4, the computer system 400 includes a processor 410. A processor 410 for a computer system 400 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. Any processor described herein is an article of manufacture and/or a machine component. A processor for a computer system 400 is configured to execute software instructions to perform functions as described in the various embodiments herein. A processor for a computer system 400 may be a general-purpose processor or may be part of an application specific integrated circuit (ASIC). A processor for a computer system 400 may also be a microprocessor, a microcomputer, a processor chip, a controller, a microcontroller, a digital signal processor (DSP), a state machine, or a programmable logic device. A processor for a computer system 400 may also be a logical circuit, including a programmable gate array (PGA) such as a field programmable gate array (FPGA), or another type of circuit that includes discrete gate and/or transistor logic. A processor for a computer system 400 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 400 includes a main memory 420 and a static memory 430 that can communicate with each other via a bus 408. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 400 may further include a video display unit 450, such as a liquid crystal display (LCD), an organic light emitting diode (OLED), a flat panel display, a solid-state display, or a cathode ray tube (CRT). Additionally, the computer system 400 may include an input device 460, such as a keyboard/virtual keyboard or touch-sensitive input screen or speech input with speech recognition, and a cursor control device 470, such as a mouse or touch-sensitive input screen or pad. The computer system 400 can also include a disk drive unit 480, a signal generation device 490, such as a speaker or remote control, and a network interface device 440.

In an embodiment, as depicted in FIG. 1C, the disk drive unit 480 may include a computer-readable medium 482 in which one or more sets of instructions 484, e.g. software, can be embedded. Sets of instructions 484 can be read from the computer-readable medium 482. Further, the instructions 484, when executed by a processor, can be used to perform one or more of the methods and processes as described herein. In an embodiment, the instructions 484 may reside completely, or at least partially, within the main memory 420, the static memory 430, and/or within the processor 410 during execution by the computer system 400.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 482 that includes instructions 484 or receives and executes instructions 484 responsive to a propagated signal; so that a device connected to a network 401 can communicate video or data over the network 401. Further, the instructions 484 may be transmitted or received over the network 401 via the network interface device 440.

Figure 5:
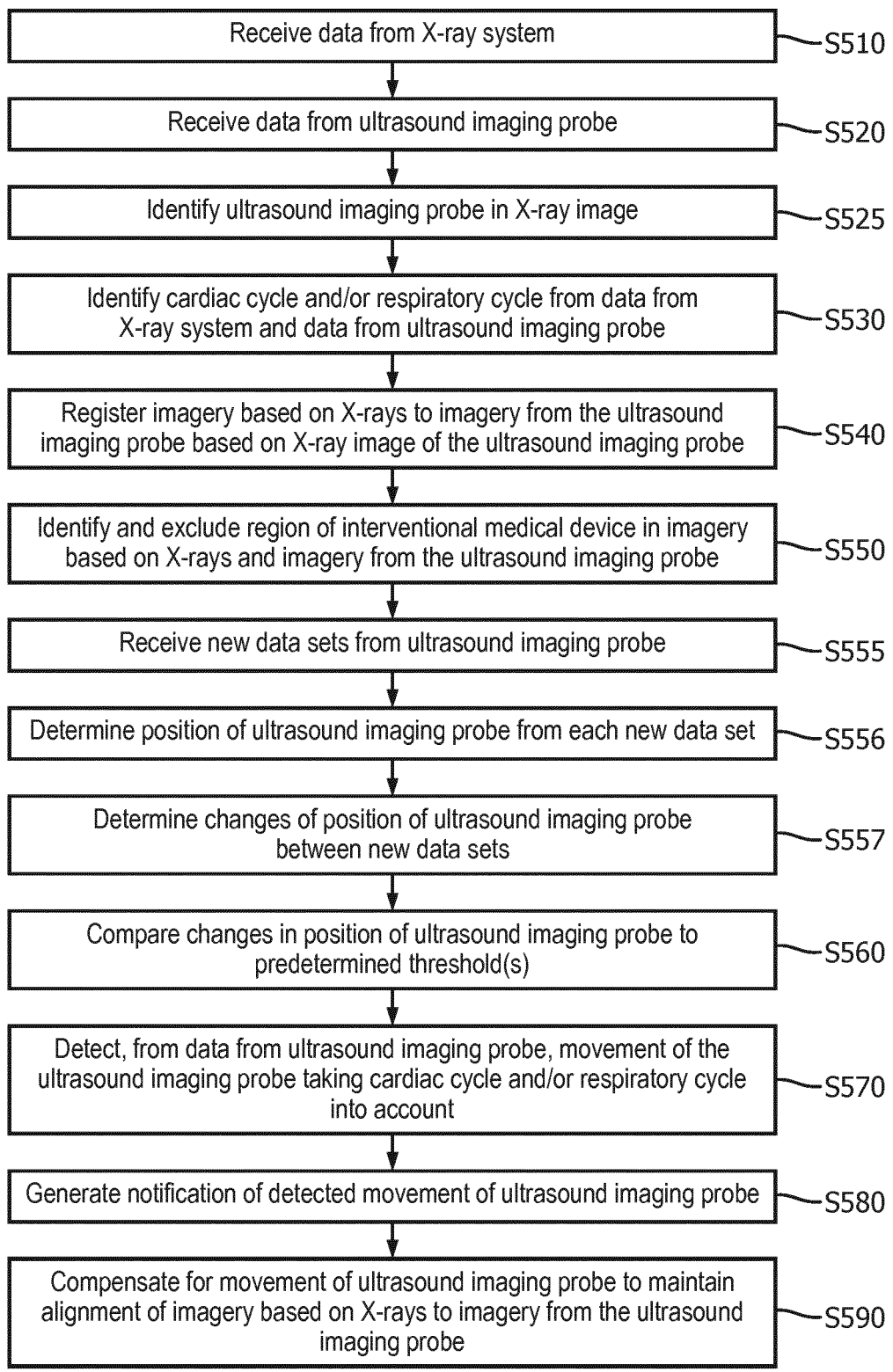
FIG. 5 illustrates a process for multi-modal imaging alignment, in accordance with a representative embodiment.

FIG. 5 illustrates a process for multi-modal imaging alignment, in accordance with a representative embodiment.

At S510, data is received from an X-Ray system such as the X-Ray emitter 372. The data may be received by the alignment system 390. The data may be X-Ray imagery, raw data that can be used to create X-Ray imagery, or both. The X-Ray imagery is imagery of a patient and includes visualizations of the interventional medical device 355 entirely or partially in the patient, and may also include imagery of the ultrasound imaging probe 356. As noted from the outset however, the X-Ray imaging by an X-Ray system is not the basis of determining movement of the ultrasound imaging probe 356 in multi-modal imaging alignment.

Rather, data received from the ultrasound imaging probe 356 at S520 is the basis of detecting movement of the ultrasound imaging probe 356. The data received from the ultrasound imaging probe 356 at S520 may be ultrasound imagery, raw data that can be used to create ultrasound imagery, or both. The ultrasound imagery is also imagery of a patient and may include visualizations of the interventional medical device 355 entirely or partially in the patient.

At S525, the ultrasound imaging probe is identified in the X-Ray imagery.

At S530, a cardiac cycle and/or a respiratory cycle are identified from the data received from the X-Ray system and/or from the data received from the ultrasound imaging probe 356.

At S540, imagery based on the X-Rays is registered to imagery from the ultrasound imaging probe 356. Registration involves aligning the same subject matter in the different imaging modes, and may involve matching one coordinate system to another, matching landmarks in one imaging mode to the same landmarks in the other imaging mode, resizing one imaging mode to match the size of the other imaging mode, or other known forms of establishing alignment between two separate images of the same scene. Imagery from one mode may be designated reference imagery or fixed imagery, and geometric transformations or local displacements can be applied to the other imagery from the other mode so that the imagery from the two imaging modes aligns. As noted previously, multi-modal imaging alignment addresses situations such as when the registration at S540 becomes outdated such as when movement of the ultrasound imaging probe 356 is detected.

At S550, the process of FIG. 5 includes identifying and excluding a region that includes the interventional medical device 355. The region that includes the interventional medical device 355 can be identified in either or both of the imagery based on X-Rays and the imagery from the ultrasound imaging probe 356.

At S555, new data sets are received from the ultrasound imaging probe 356. The process up to and including S550 may be considered a form of background to the process after S550 in the sense that the initial registration at S540 that may be become stale is the, or one of the, central concern(s) addressed by multi-modal imaging alignment described herein. The new data sets from the ultrasound imaging probe at S555 are the data sets from which movement of the ultrasound imaging probe is detected.

At S556, the position of the ultrasound imaging probe 356 is determined from each new data set. At S557, changes of position of the ultrasound imaging probe are determined as between two of the new data sets. For example, each time a new data set is acquired at S555, the position of the ultrasound imaging probe 356 determined at S556 from the new data set may be compared with the position in the immediately previous data set, or another previous data set such as from a predetermined period prior to the new data set, or from a predetermined number of data sets before the new data set.

At S560, changes in the position of the ultrasound imaging probe 356 are compared to one or more predetermined thresholds. For example, the positions of the ultrasound imaging probe 356 may be identified from different image frames based on the data from the ultrasound imaging probe 356, such as by rotations or offsets in landmarks or other mechanisms described above. The different image frames may be consecutive, or may be offset by a specified amount of time or number of intervening image frames. The thresholds may be binary thresholds, or may be a sliding scale that includes different thresholds each with a different meaning or consequence such as the level of resultant notification. Once the amount of movement is determined, the comparison at S560 may be a relatively simple matter that involves comparing the amount of determined movement with the one or more thresholds.

At S570, movement of the ultrasound imaging probe 356 is formally detected from the data from the ultrasound imaging probe 356. The detection at S570 is based on the changes in position at S560 being more than de minimis, and also takes into account the cardiac cycle and/or respiratory cycle from S530. Thus, detection of movement of the ultrasound imaging probe from data from the ultrasound imaging probe at S570 involves the formal confirmation of movement that reflects, for example, that imagery based on X-Rays may be outdated such that the registration of imagery at S540 is outdated.

At S580, a notification is generated to notify of the detected movement of the ultrasound imaging probe 356.

At S590, the process of FIG. 5 compensates for movement of the ultrasound imaging probe to maintain alignment of the imagery based on the X-Rays to the imagery from the ultrasound imaging probe. Compensation may involve shifting image information on one or more than one cartesian axis or axes, or rotating image information about an axis or more than one axes. Although not shown in FIG. 5, the registration at S540 may be performed again based on the compensation at S590.

Figure 6:
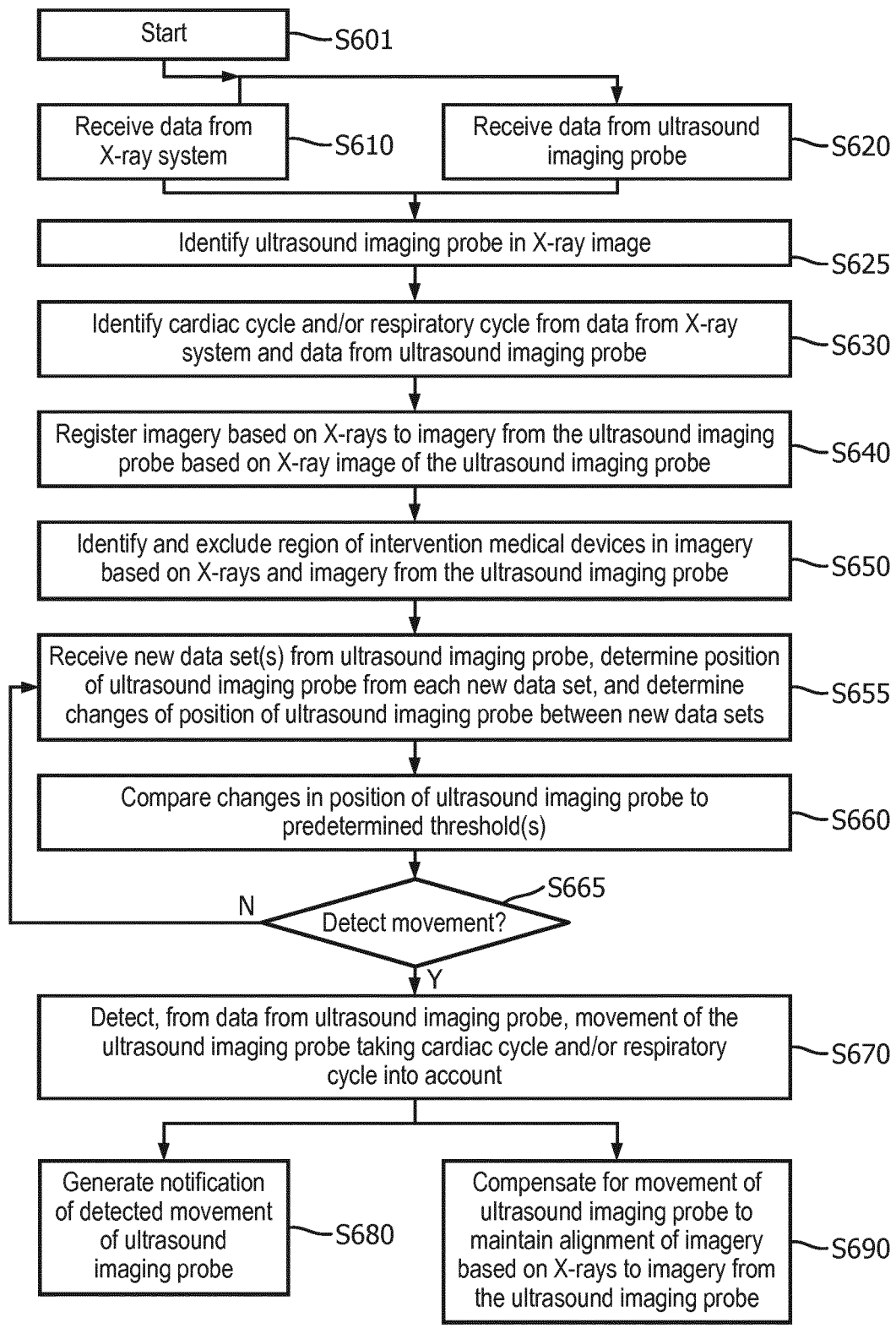
FIG. 6 illustrates another process for multi-modal imaging alignment, in accordance with a representative embodiment.

FIG. 6 illustrates another process for multi-modal imaging alignment, in accordance with a representative embodiment.

The process of FIG. 6 starts at S601. At S610, data from the X-Ray system is received, and at S620 data from the ultrasound imaging probe 356 is received. Receipt of data at S610 and S620 may be simultaneous as shown, or may be sequential, or may overlap such that the receipt is partly simultaneous and partly sequential.

At S625, the ultrasound imaging probe 356 is identified in the X-Ray image. At S630, the cardiac cycle and/or the respiratory cycle are identified from data from the X-Ray system and data from the ultrasound imaging probe 356.

At S640, imagery based on X-Rays is registered to imagery from the ultrasound imaging probe 356 based on the X-Ray imagery that includes the identified ultrasound imaging probe 356.

At S650, a region of (around) the interventional medical device 355 is identified and excluded in imagery based on X-Rays and imagery from the ultrasound imaging probe 356.

At S655, new data set(s) are received from the ultrasound imaging probe 356, the position of the ultrasound imaging probe 356 is determined from each new data set, and changes of position of the ultrasound imaging probe 356 are determined between two of the new data sets.

At S660, a change in the position of the ultrasound imaging probe is compared to a predetermined threshold. The change may be any observed motion between sequential image frames, no matter how small.

At S665, a determination is made as to whether movement is detected. Movement is detected when the changes in position at S660 are above a threshold. If no movement is detected (S665=No), the process returns to S655 to again receive data from the X-Ray system and the ultrasound imaging probe 356.

If movement is detected (S665=Yes), at S670 movement of the ultrasound imaging probe is detected taking into account the cardiac cycle and/or the respiratory cycle. That is, movement of the probe based on natural heart motion and/or natural or assisted breathing motion, may be excluded, offset, or otherwise factored out.

At S680, a notification of the detected movement of the ultrasound imaging probe 356 is generated. At S690, movement of the ultrasound imaging probe is compensated to maintain alignment of the imagery based on X-Rays to imagery from the ultrasound imaging probe 356. Notification at S680 and compensation at S690 may be simultaneous as shown, or may be sequential, or may overlap such that the notification and compensation are partly simultaneous and partly sequential.

Figure 7:
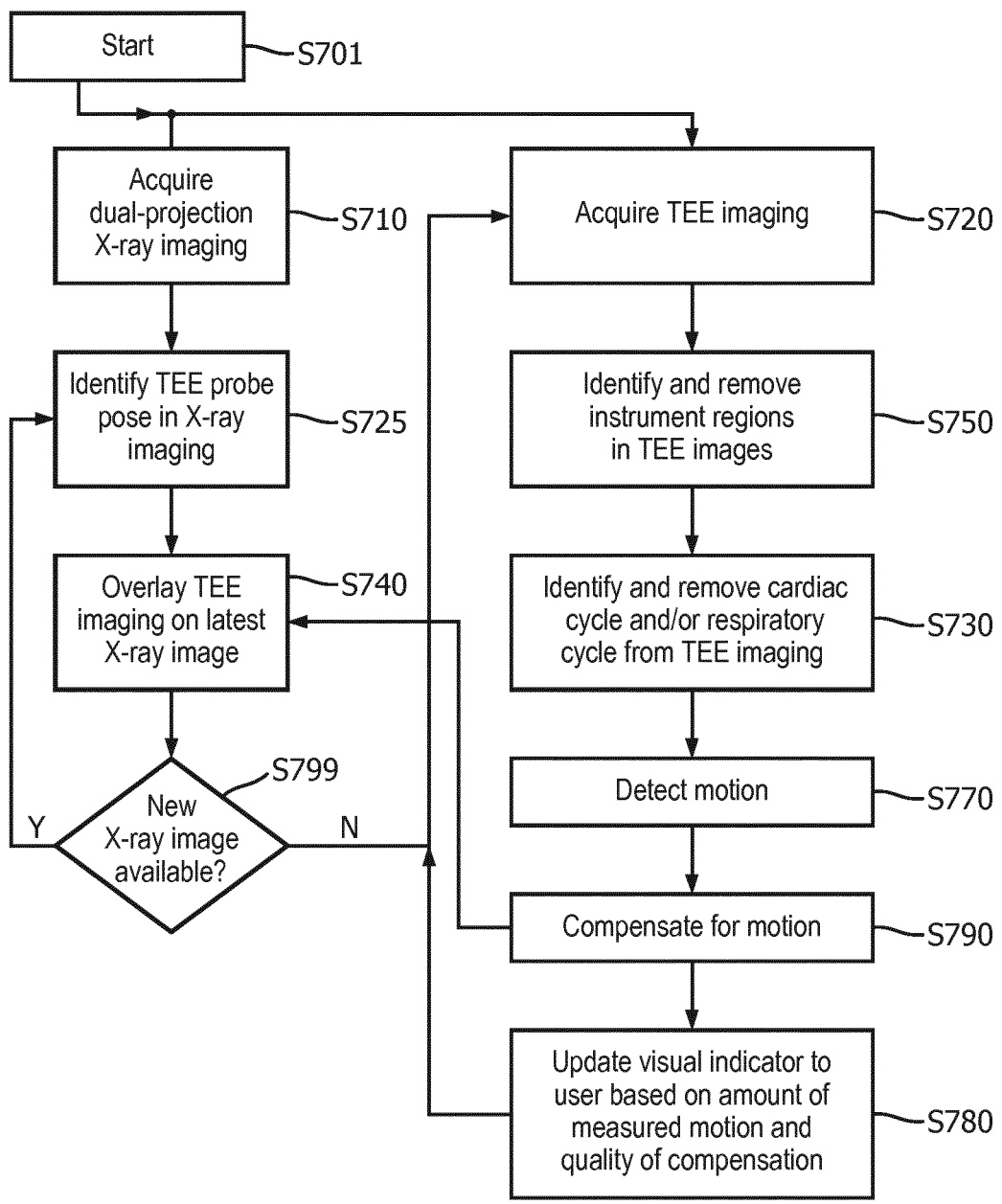
FIG. 7 illustrates another process for multi-modal imaging alignment, in accordance with a representative embodiment.

FIG. 7 illustrates another process for multi-modal imaging alignment, in accordance with a representative embodiment. In FIG. 7, element numbers may be out of numerical order in order to clearly draw correlations with element numbers in other embodiments. Nevertheless, the flow shown in FIG. 7 is representative of aspects of the process for multi-modal imaging alignment in the embodiment shown in FIG. 7.

The process of FIG. 7 starts at S701. At S710, dual-projection X-Ray imaging is acquired. Dual projection X-Ray imaging is X-Ray imaging projected from two planes, and this may be performed initially whereas subsequent X-Ray imaging may be from a single plane. At S720, TEE imaging is acquired from a TEE probe. Receipt of dual-projection X-Ray imaging at S710 and TEE imaging at S720 may be simultaneous as shown, or may be sequential, or may overlap such that the receipt is partly simultaneous and partly sequential.

At S725, the pose of the TEE probe is identified in the X-Ray imaging. The pose of the TEE probe includes the location and orientation of the TEE probe.

At S740, the TEE imaging is overlaid on the latest X-Ray Image. A determination at S799 is made as to whether a new X-Ray image is available, and if not (S799=No), the process returns to S720 to acquire new TEE imaging. If a new X-Ray image is available (S799=Yes), the process returns to S725 to again identify the TEE probe pose in the new X-Ray image.

At S750, an instrument region is identified and removed from the TEE images acquired at S720. At S730, cardiac motions and breathing motions are removed from the TEE imaging. At S770, motion is detected, and at S790 the detected motion is compensated. The compensated motion output after S790 is provided both for the overlaying on the latest X-Ray image at S740, and to update a visual indicator provided to the user to reflect the amount of measured motion compensated at S790 and the quality of the compensation. After updating the visual indicator at S790, the process returns to S720 to again acquire TEE imaging.

As shown in FIG. 7 and described above, two parallel processes may be performed with multiple loops in a recursive pattern. Accordingly, an initial X-Ray image acquired as a dual-projection X-Ray image at S710 may be followed with single-projection X-Ray images (not shown), such that the identification of the TEE probe at S725 is performed each time a new X-Ray image is available (S799=Yes). The TEE processing from S720 to S780 may be performed also in a loop so that compensated motion is repeatedly used to overlay new TEE imaging on the latest X-Ray image at S740 and update the visual indicator at S780 before again acquiring new TEE imaging at S720.

As noted above, element numbers in FIG. 7 may appear out of numerical order, but this is done in order to clearly draw correlations with similar element numbers in other embodiments. The different order of steps reflects variability in processing steps for multi-modal imaging alignment, in that steps shown in the various embodiments may be performed in a different order, not at all, or with additional intervening steps and processes (not shown) performed in between. Accordingly, multi-modal imaging alignment provides mechanisms for identifying and addressing movement of the ultrasound probe. Measured movement may be compared to thresholds, and subject to correction to remove or otherwise account for effects from a respiratory cycle and/or a cardiac cycle. If the measured movement is significant enough to warrant remediation, an operator can be provided with a notification including a variable notification that reflects the degree of movement, and/or the movement can be compensated to adjust the imagery from the ultrasound to again match the geometry of the imagery from the X-ray.

Although multi-modal imaging alignment has been described with reference to several exemplary embodiments, it is understood that the words that have been used are words of description and illustration, rather than words of limitation. Changes may be made within the purview of the appended claims, as presently stated and as amended, without departing from the scope and spirit of multi-modal imaging alignment in its aspects. Although multi-modal imaging alignment has been described with reference to particular means, materials and embodiments, multi-modal imaging alignment is not intended to be limited to the particulars disclosed; rather multi-modal imaging alignment extends to all functionally equivalent structures, methods, and uses such as are within the scope of the appended claims.

For example, FIG. 3 shows an alignment system 390 separate from the central station 360 and the X-Ray emitter 372. However, alignment can be performed by one or the other of the central station 360 or equivalent or X-Ray emitter or equivalent.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A controller for maintaining alignment of X-Ray imagery and ultrasound imagery, the controller comprising:
a memory configured to store instructions; and
a processor configured to execute the instructions, and, when executed by the processor, the instructions cause the controller to:
receive X-Ray imaging data from an X-Ray system configured to perform X-Ray imaging, wherein the X-Ray imaging data comprises X-Ray imagery of an anatomical region,
receive ultrasound imaging data from an ultrasound imaging probe configured to perform ultrasound imaging, wherein the ultrasound imaging data comprises ultrasound imagery of the anatomical region,
register, in a common coordinate system, the X-Ray imagery of the anatomical region from the X-Ray system to the ultrasound imagery of the anatomical region from the ultrasound imaging probe based on an X-Ray image of the X-Ray imagery,
receive a new ultrasound data set from the ultrasound imaging probe,
detect movement of the ultrasound imaging probe based on a change in position of the ultrasound imaging probe between the new ultrasound data set and a previous ultrasound data set received from the ultrasound imaging probe,
measure the movement of the ultrasound imaging probe, and
without receiving new X-Ray imaging data from the X-Ray system, compensate for the movement of the ultrasound imaging probe by re-aligning the ultrasound imagery of the anatomical region with the X-Ray imagery of the anatomical region such that a new correspondence is established between the ultrasound imagery of the anatomical region and the X-Ray imagery of the anatomical region by adjusting the ultrasound imagery of the anatomical region relative to the common coordinate system using the measured movement of the ultrasound imaging probe.

2. The controller of claim 1, wherein, when executed by the processor, the instructions further cause the controller to:
determine that the movement of the ultrasound imaging probe exceeds a predetermined threshold, and
generate a notification based on detecting the movement of the ultrasound imaging probe.

3. The controller of claim 2, wherein:
the predetermined threshold varies among a plurality of predetermined thresholds, and
the notification varies based on an amount of the movement of the ultrasound imaging probe.

4. The controller of claim 3, wherein, when executed by the processor, the instructions further cause the controller to:
measure the amount of the movement of the ultrasound imaging probe, and
wherein the compensated movement is to correct a registration mismatch between the X-Ray imagery of the anatomical region from the X-Ray system and the ultrasound imagery of the anatomical region from the ultrasound imaging probe.

5. The controller of claim 1, wherein, when executed by the processor, the instructions further cause the controller to:
detect the movement of the ultrasound imaging probe based on analysis of a cineloop from the ultrasound imaging probe.

6. The controller of claim 5, wherein, when executed by the processor, the instructions further cause the controller to:
identify a region in which an interventional medical device is moved in the cineloop from the ultrasound imaging probe; and
exclude movement within the region from detection of the movement of the ultrasound imaging probe.

7. The controller of claim 5, wherein, when executed by the processor, the instructions further cause the controller to:
identify a three-dimensional cardiac cycle over time that affects the ultrasound imaging probe as a dataset of a four-dimensional cardiac cycle; and
detect movement of the ultrasound imaging probe between cycles of the four-dimensional cardiac cycle using the dataset.

8. The controller of claim 5, wherein, when executed by the processor, the instructions further cause the controller to:
identify a respiratory cycle that affects the ultrasound imaging probe; and
identify and remove periodicity due to respiration in the respiratory cycle.

9. The controller of claim 8, wherein, when executed by the processor, the instructions further cause the controller to:
compensate for respiratory motion based on input received from an external respiration device.

10. The controller of claim 1, wherein, when executed by the processor, the instructions further cause the controller to:
detect the movement of the ultrasound imaging probe based on an external sensor.

11. The controller of claim 1, wherein, when executed by the processor, the instructions further cause the controller to:
align the X-Ray imagery of the anatomical region from the X-Ray system and the ultrasound imagery of the anatomical region from the ultrasound imaging probe based on compensating for the movement of the ultrasound imaging probe.

12. A method for maintaining alignment of X-Ray imagery and ultrasound imagery, the method comprising:
receiving X-Ray imaging data from an X-Ray system configured to perform X-Ray imaging, wherein the X-Ray imaging data comprises X-Ray imagery of an anatomical region;
receiving ultrasound imaging data from an ultrasound imaging probe configured to perform ultrasound imaging, wherein the ultrasound imaging data comprises ultrasound imagery of the anatomical region;
registering, in a common coordinate system, the X-Ray imagery of the anatomical region from the X-Ray system to the ultrasound imagery of the anatomical region from the ultrasound imaging probe based on an X-Ray image of the X-Ray imagery;
receiving a new ultrasound data set from the ultrasound imaging probe;
detecting movement of the ultrasound imaging probe based on a change in position of the ultrasound imaging probe between the new ultrasound data set and a previous ultrasound data set received from the ultrasound imaging probe;
measuring the movement of the ultrasound imaging probe; and
without receiving new X-Ray imaging data from the X-Ray system, compensating for the movement of the ultrasound imaging probe by re-aligning the ultrasound imagery of the anatomical region with the X-Ray imagery of the anatomical region such that a new correspondence is established between the ultrasound imagery of the anatomical region and the X-Ray imagery of the anatomical region by adjusting the ultrasound imagery of the anatomical region relative to the common coordinate system using the measured movement of the ultrasound imaging probe.

13. The method of claim 12, further comprising:
determining that the movement of the ultrasound imaging probe exceeds a predetermined threshold, and
generating a notification based on detecting the movement of the ultrasound imaging probe.

14. The method of claim 13, wherein:
the predetermined threshold varies among a plurality of predetermined thresholds, and
the notification varies based on an amount of the movement of the ultrasound imaging probe.

15. The method of claim 12, wherein:
the ultrasound imaging probe comprises a transesophageal echocardiography (TEE) probe,
the ultrasound imagery of the anatomical region from the ultrasound imaging probe comprises TEE imagery, and
the ultrasound imaging data from the ultrasound imaging probe comprises the TEE imagery.

16. The method of claim 12, further comprising:
fusing the X-Ray imagery of the anatomical region from the X-Ray system and the ultrasound imagery of the anatomical region from the ultrasound imaging probe based on the compensating for the movement of the ultrasound imaging probe.

17. The method of claim 12,
wherein the movement of the ultrasound imaging probe is detected based on analysis of a cineloop from the ultrasound imaging probe.

18. A system for maintaining alignment of X-Ray imagery and ultrasound imagery, comprising:
an X-Ray system configured to acquire X-Ray imaging data;
an ultrasound imaging probe configured to acquire ultrasound imaging data; and
a controller including a memory that stores instructions and a processor that executes the instructions, and, when executed by the processor, the instructions cause the controller to:
receive the X-Ray imaging data from the X-Ray system, wherein the received X-Ray imaging data comprises X-Ray imagery of an anatomical region,
receive the ultrasound imaging data from the ultrasound imaging probe, wherein the received ultrasound imaging data comprises ultrasound imagery of the anatomical region,
register, in a common coordinate system, the X-Ray imagery of the anatomical region from the X-Ray system to ultrasound imagery of the anatomical region from the ultrasound imaging probe based on an X-Ray image of the X-Ray imagery,
receive a new ultrasound data set from the ultrasound imaging probe,
detect movement of the ultrasound imaging probe based on a change in position of the ultrasound imaging probe between the new ultrasound data set and a previous ultrasound data set received from the ultrasound imaging probe,
measure the movement of the ultrasound imaging probe, and
without receiving new X-Ray imaging data from the X-Ray system, compensate for the movement of the ultrasound imaging probe by re-aligning the ultrasound imagery of the anatomical region with the X-Ray imagery of the anatomical region such that a new correspondence is established between the ultrasound imagery of the anatomical region and the X-Ray imagery of the anatomical region by adjusting the ultrasound imagery of the anatomical region relative to the common coordinate system using the measured movement of the ultrasound imaging probe.

* * * * *